(12) United States Patent
D'Anello et al.

(10) Patent No.: US 8,399,668 B2
(45) Date of Patent: Mar. 19, 2013

(54) PROCESS FOR THE PREPARATION OF 5-(2-AMINO-PYRIMIDIN-4-YL)-2-ARYL-1H-PYRROLE-3-CARBOXAMIDES

(75) Inventors: Matteo D'Anello, Novate Milanese (IT); Carlo Battistini, Novate Milanese (IT); Maria Gioia Fornaretto, Milan (IT); Ermes Vanotti, Milan (IT)

(73) Assignee: Nerviano Medical Sciences S. R. L., Nerviano (MI) (IT)

( * ) Notice: Subject to any disclaimer, the term of this patent is extended or adjusted under 35 U.S.C. 154(b) by 278 days.

(21) Appl. No.: 12/989,518

(22) PCT Filed: Apr. 30, 2009

(86) PCT No.: PCT/EP2009/055262
§ 371 (c)(1),
(2), (4) Date: Oct. 25, 2010

(87) PCT Pub. No.: WO2009/133170
PCT Pub. Date: Nov. 5, 2009

(65) Prior Publication Data
US 2011/0040090 A1    Feb. 17, 2011

(30) Foreign Application Priority Data
Apr. 30, 2008  (EP) .................................... 08155501

(51) Int. Cl.
*C07D 403/04*    (2006.01)

(52) U.S. Cl. ......... 544/331; 548/560; 548/561; 548/562
(58) Field of Classification Search .................. 544/331; 548/560, 561, 562
See application file for complete search history.

(56) References Cited

FOREIGN PATENT DOCUMENTS
WO    WO 2007/110344 A1    10/2007

*Primary Examiner* — Deepak Rao
(74) *Attorney, Agent, or Firm* — Scully, Scott, Murphy & Presser, P.C.

(57) ABSTRACT

The present invention relates to a process for the preparation of 5-(2-amino-pyrimidin-4-yl)-2-aryl-1H-pyrrole-3-carboxamides and to the useful intermediate compounds of such process. 5-(2-Amino-pyrimidin-4-yl)-2-aryl-1H-pyrrole-3-carboxamides are described and claimed in WO2007110344, which also discloses processes for their preparation. These compounds can be advantageously prepared through a process which allows to obtain the desired products in high yields and purity and with a limited number of steps. The synthesis is starting from a cyano pyrrole derivative, and is characterized from the final hydrolysis of 5-(2-amino-pyrimidin-4-yl)-2-aryl-1H-pyrrole-3-carbonitrile. The compounds prepared according to the process of the present invention are endowed with protein kinase inhibiting activity and, more particularly, Cdc7 or Cdc7/Cdks inhibiting activity. The compounds are therefore useful in the treatment of a variety of cancers, cell proliferative disorders and diseases associated with protein kinases.

13 Claims, No Drawings

PROCESS FOR THE PREPARATION OF 5-(2-AMINO-PYRIMIDIN-4-YL)-2-ARYL-1H-PYRROLE-3-CARBOXAMIDES

The present invention relates to a process for the preparation of 5-(2-amino-pyrimidin-4-yl)-2-aryl-1H-pyrrole-3-carboxamides and to the useful intermediate compounds of such process.

WO2007110344 describes and claims heteropentacycles, processes for their preparation, pharmaceutical compositions comprising them and their use as therapeutic agents, particularly in the treatment of cancer and cell proliferation disorders.

Representative heteropentacycle compounds, optionally in the form of pharmaceutically acceptable salts, are for example:
5-(2-amino-pyrimidin-4-yl)-2-phenyl-1H-pyrrole-3-carboxylic acid amide;
5-(2-amino-pyrimidin-4-yl)-2-o-tolyl-1H-pyrrole-3-carboxylic acid amide;
5-(2-amino-pyrimidin-4-yl)-2-(4-fluoro-2-methyl-phenyl)-1H-pyrrole-3-carboxylic acid amide;
5-(2-amino-pyrimidin-4-yl)-2-(2,3-dimethyl-phenyl)-1H-pyrrole-3-carboxylic acid amide;
5-(2-amino-pyrimidin-4-yl)-2-(2,3-difluoro-phenyl)-1H-pyrrole-3-carboxylic acid amide;
5-(2-amino-pyrimidin-4-yl)-2-(2,4-difluoro-phenyl)-1H-pyrrole-3-carboxylic acid amide;
5-(2-amino-pyrimidin-4-yl)-2-(2,5-difluoro-phenyl)-1H-pyrrole-3-carboxylic acid amide;
5-(2-amino-pyrimidin-4-yl)-2-(2-chloro-phenyl)-1H-pyrrole-3-carboxylic acid amide;
5-(2-amino-pyrimidin-4-yl)-2-(2-chloro-4-fluoro-phenyl)-1H-pyrrole-3-carboxylic acid amide;
5-(2-amino-pyrimidin-4-yl)-2-(2,4-dichloro-phenyl)-1H-pyrrole-3-carboxylic acid amide;
5-(2-amino-pyrimidin-4-yl)-2-(2-fluoro-4-methyl-phenyl)-1H-pyrrole-3-carboxylic acid amide;
5-(2-amino-pyrimidin-4-yl)-2-(2,3-dichloro-phenyl)-1H-pyrrole-3-carboxylic acid amide;
5-(2-amino-pyrimidin-4-yl)-2-(2-fluoro-3-methoxy-phenyl)-1H-pyrrole-3-carboxylic acid amide and
5-(2-amino-pyrimidin-4-yl)-2-(2-fluoro-4-chloro-phenyl)-1H-pyrrole-3-carboxylic acid amide.

Such compounds are endowed with protein kinase inhibiting activity and, more particularly, Cdc7 or Cdc7/Cdks inhibiting activity.

More specifically, the compounds prepared according to this invention are useful in the treatment of a variety of cancers and of cell proliferative disorders.

The compounds may be also active as inhibitors of other protein kinases and thus be effective in the treatment of diseases associated with other protein kinases.

These compounds, and analogues thereof, can be prepared according to a known chemical process comprising, essentially, the condensation reaction between a carboxylic acid derivative with either an activated form of ammonia, or with an amine to give the desired amide. Such carboxylic acid derivative, in its turn, is prepared according to a procedure comprising the coupling of a haloketone with a beta-ketoester, a Hantzsch reaction and a hydrolysis. For reference, this process is described in the above mentioned patent application WO2007110344.

In this respect, we have now surprisingly found that said heteropentacycle compounds can be advantageously prepared through a process which allows to obtain the desired products in high yields and purity and with a limited number of steps.

Therefore, it is a first object of the present invention a process for preparing a 5-(2-amino-pyrimidin-4-yl)-2-aryl-1H-pyrrole-3-carboxamides of the formula (I):

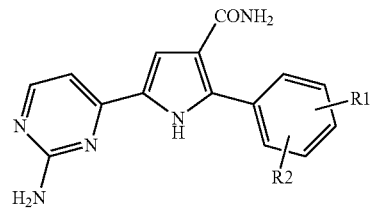

wherein $R_1$ and $R_2$ independently represent hydrogen or halogen atom or alkyl, cycloalkyl, aryl, aroyl, carboxyl esters, cyano or nitro group, which process comprises:

(a) reacting a pyrrole of the formula (II):

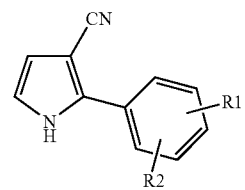

wherein $R_1$ and $R_2$ are as defined above, with acetyl chloride in the presence of a Lewis acid;

(b) reacting the resultant compound of the formula (III):

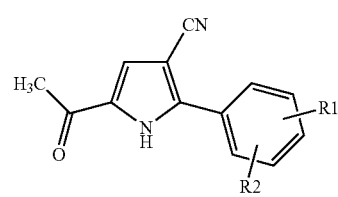

wherein $R_1$ and $R_2$ are as defined above, with a dialkyl acetal of N,N-dimethylformamide, (c) reacting the resultant enaminone of the formula (IV):

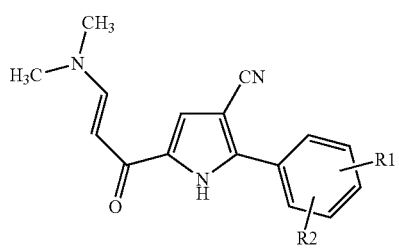

wherein $R_1$ and $R_2$ are as defined above, with guanidine or a salt thereof, and then, (d) hydrolizing the cyano group of the resultant compound of the formula (V)

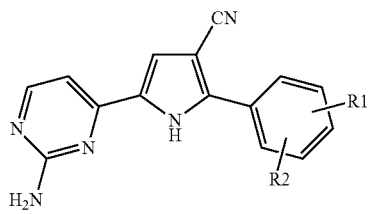

V wherein $R_1$ and $R_2$ are as defined above in acidic conditions, so as to obtain the amide of the formula (I), as defined above in salt form;

and, if desired, converting the resultant salt into the free base in basic conditions.

It is a further object of the present invention a process for preparing a 5-(2-amino-pyrimidin-4-yl)-2-aryl-1H-pyrrole-3-carboxamide of the formula (I) as above defined, which process comprises the hydrolysis of the cyano group of the compound of the formula (V) as above defined in acidic conditions, and then, if desired, the conversion of the resultant salt form the amide of the formula (I) as defined above into the free base in basic conditions.

The final compounds may be isolated and purified using conventional procedures, for example chromatography and/or crystallization and salt formation.

The carboxamides of the formula (I) as defined above can be converted into pharmaceutically acceptable salts. The carboxamides of the formula (I) as defined above, or the pharmaceutically acceptable salts thereof, can be subsequently formulated with a pharmaceutically acceptable carrier or diluent to provide a pharmaceutical composition.

Moreover, it is another object of the present invention an intermediate compound of the formula III, IV or V as defined above, as well as the processes for their preparation.

In the present specification, the terms
"halogen" refers to bromo, chloro, iodo or fluoro, more preferably chloro or fluoro;
"alkyl" refers to straight or branched saturated aliphatic hydrocarbyl groups having from 1 to 6 carbon atoms; this term is exemplified by groups such as methyl, ethyl, n-propyl, iso-propyl, n-butyl, isobutyl, sec-butyl, t-butyl, n-pentyl, n-hexyl, and the like;
"cycloalkyl" refers to cyclic alkyl groups of from 3 to 10 carbon atoms having single or multiple cyclic rings including, by way of example, adamantyl, cyclopropyl, cyclobutyl, cyclopentyl, cyclohexyl, cyclooctyl and the like;
"aryl" refers to an aromatic carbocyclic group of from 6 to 14 carbon atoms having a single ring (e.g. phenyl) or multiple condensed rings (e.g. naphthyl or anthryl) which condensed rings may or may not be aromatic (e.g. 2-benzoxazolinone, 2H-1,4-benzoxazin-3(4H)-one-7-yl, and the like) provided that the point of attachment is at an aromatic carbon atom; preferred aryls include phenyl and naphthyl; in the name of the compounds of the formula I, aryl is a phenyl substituted with $R_1$ and $R_2$ as defined above;
"aroyl" refers to arylcarbonyl Ar—CO— wherein aryl is as defined herein;
"carboxyl esters" refers to the groups —C(O)O-alkyl, —C(O)O-aryl, wherein alkyl and aryl are as defined herein;
"cyano" or "nitrile" refer to the group —CN;
"nitro" refers to the group —$NO_2$.

The preferred compounds according to the invention are those wherein $R_1$ and $R_2$ independently represent hydrogen or halogen atoms or alkyl or alkoxy groups more preferably methyl groups, fluoro or chloro atoms.

As stated above, the present invention also provides a compound of the formula (III):

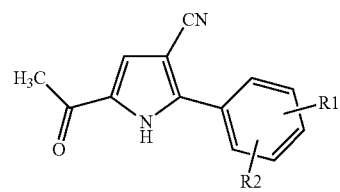

III wherein $R_1$ and $R_2$ are as defined above.

It is a further object of the present invention a process for preparing a compound of the formula (III) as defined above, by reaction of a pyrrole of the formula (II) as above defined with acetyl chloride in the presence of a Lewis acid.

The present invention also provides a compound of the formula (IV):

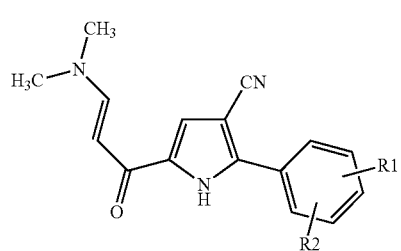

IV wherein $R_1$ and $R_2$ are as defined above.

It is still another object of the present invention a process for preparing a compound of the formula (IV) as defined above, by treatment of a compound of the formula (III) as defined above with a dialkyl acetal of N,N-dimethylformamide.

It is also provided a compound of the formula (V)

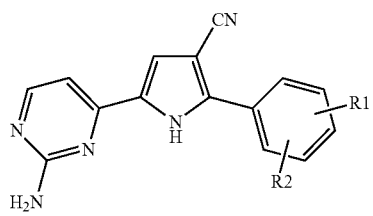

V wherein $R_1$ and $R_2$ are as defined above.

Lastly, the present invention comprises a process for preparing a compound of the formula (V) as defined above by reaction of the compound of the formula (IV) as defined above with guanidine or a salt thereof.

The acylation of a compound of the formula (II) to give a compound of the formula (III) is preferably performed with acetyl chloride in the presence of a Lewis acid, for instance aluminum trichloride or titanium tetrachloride, operating under cooling, e.g. at a temperature of from −5° C. to 0° C., or at room temperature, in an anhydrous organic solvent, e.g. dichloromethane. A similar reaction is described in *J. Het. Chem.* 1983, 20, 61.

The conversion of a compound of the formula (III) into the enaminone of the formula (IV) may be carried out using a dialkyl acetal, for instance the dimethyl acetal or diisopropyl acetal, of N,N-dimethylformamide. Preferably the reaction is carried out at a temperature between room and reflux temperature, preferably at a temperature of from 60° to 90° C., in an organic solvent such as, e.g., toluene, benzene, dichloroethane or dimethylformamide. An analogous transformation was described, for instance, in *Heterocycles* 1998, 47, 689.

The conversion of a compound of the formula (IV) into a compound of the formula (V) is carried out by reaction with guanidine, guanidine hydrochloride or guanidine carbonate. Preferably the reaction is carried out at a temperature of from 80° C. to 130° C., in an organic solvent such as, e.g., acetamide, N-methyl-2-pyrrolidone, dimethylformamide. Such kind of conversion are described in the scientific literature, for example in *J. Het. Chem.* 1989, 26, 1147.

The hydrolysis in acidic condition of the nitrile derivative of the formula (V) to yield the carboxamides of the formula (I) is preferably performed in glacial acetic acid or trifluoroacetic acid and concentrated sulfuric acid, more preferably in ratios between 1 to 1 and 5 to 1, optionally in the presence of water, at a temperature between room temperature and 120° C., in particular at a temperature of from 60° to 90° C. An analogous hydrolysis is for example described in *J. Org. Chem.* 2005, 70, 1926.

After basification with concentrated aqueous ammonia, sodium hydroxide or potassium hydroxide, the free base is filtered off as a precipitate.

The starting compounds and the reagents employed in the process of the present invention are known compounds or can be obtained from known compounds using well known methods. In particular, the starting compounds of the formula (II) as defined above are known or can be obtained with known reactions starting from known compounds, see for example the compounds and their preparations described in EP 0347,488; EP 0312,723 and EP 0358,047.

The following examples illustrate but does not limit the invention.

EXAMPLE 1

Step I 5-Acetyl-2-(2,4-dichloro-phenyl)-1H-pyrrole-3-carbonitrile (III, $R_1=R_2=Cl$)

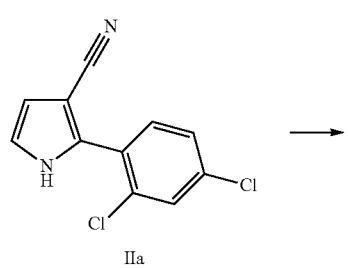

IIa

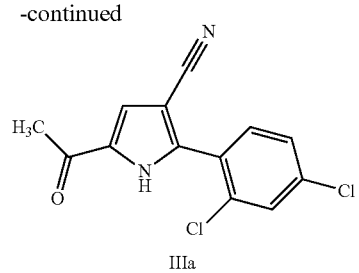

IIIa

To a mixture of 2-(2,4-dichloro-phenyl)-1H-pyrrole-3-carbonitrile (6.00 g, 25.30 mmol, see EP 0312,723) in 120 mL of dichloromethane was added acetyl chloride (3.18 g; 40.49 mmol) at room temperature, under nitrogen. The resulting mixture was cooled to +2° C. and anhydrous aluminum trichloride (8.10 g, 60.73 mmol) was added in small portions during a period of 20 minutes, keeping the internal temperature below 5° C. Upon complete addition, the mixture was brought to room temperature and allowed to stir for 3 hours. Then, the mixture was slowly poured in a solution of ice-cooled 2M HCl (120 mL) and isopropanol (28 mL). The aqueous layer was separated and extracted twice with a mixture of dichloromethane (120 mL) and isopropanol (28 mL). The combined organic extracts were concentrated under reduced pressure to slurry, which was treated under stirring with isopropanol (30 mL) and diluted with water (60 mL) at room temperature. The solid was collected by suction and dried under vacuum at +50° C. to afford the 6.51 g of product as white, fluffy crystals. Yield=92%.

$^1$H-NMR (DMSOd$_6$), δ ppm: 2.45 (s, 3H) 7.59 (m, 3H) 7.86 (dd, 1H) 13.05 (bs, 1H).

HRMS (M+H)$^+$ calcd: 279.0087. found: 279.0091.

Step II 2-(2,4-Dichloro-phenyl)-5-((E)-3-dimethylamino-acryloyl)-1H-pyrrole-3-carbonitrile (IV, $R_1=R_2=Cl$)

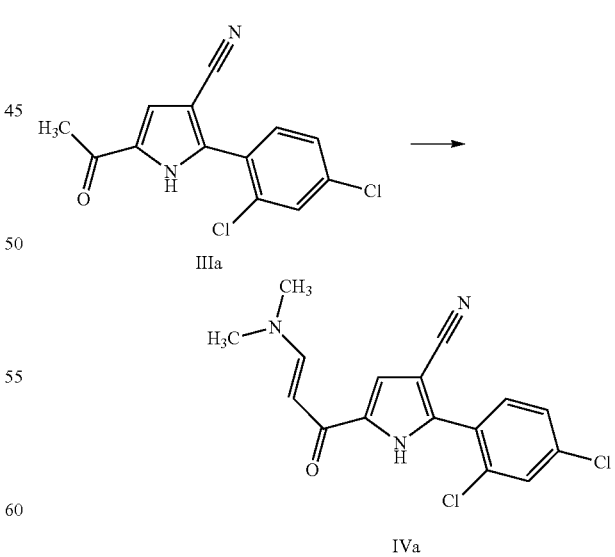

To a suspension of 5-acetyl-2-(2,4-dichloro-phenyl)-1H-pyrrole-3-carbonitrile (6.2 g, 22.21 mmol) in 155 mL of toluene was added N,N-dimethylformamide diisopropyl acetal (18.6 mL; 88.85 mmol). The mixture was allowed to stir for 34 hours at 70° C. Then, a further amount of reagent was added (4.6 mL; 22.21 mmol) and the mixture was heated to 80° C. for additional 18 hours under efficient stirring.

After cooling to room temperature, the solid was collected by suction, washed with 25 mL of toluene and dried in the air to yield 6.8 g of product as white solid. Yield=91%.

$^1$H-NMR (DMSOd$_6$), δ ppm: 2.90 (m, 3H) 3.15 (bs, 3H) 5.74 (d, 1H) 7.37 (d, 1H) 7.57 (m, 2H) 7.69 (d, 1H) 7.82 (dd, 1H) 12.64 (bs, 1H).

HRMS (M+H)$^+$ calcd: 334.0509. found: 334.0513.

Step III 5-(2-Amino-pyrimidin-4-yl)-2-(2,4-dichloro-phenyl)-1H-pyrrole-3-carbonitrile (V, R$_2$=R$_2$=Cl)

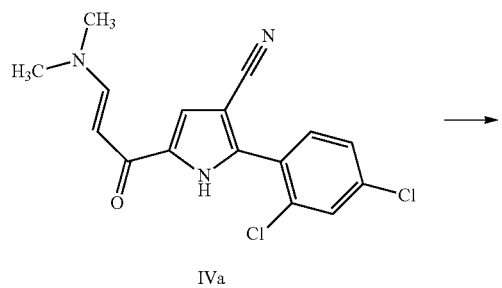

IVa

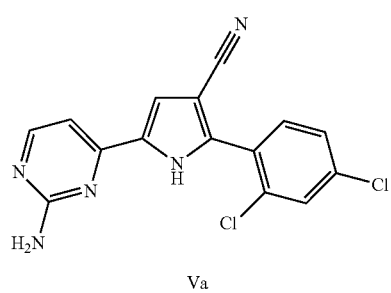

Va

To a suspension of 2-(2,4-dichloro-phenyl)-5-((E)-3-dimethylamino-acryloyl)-1H-pyrrole-3-carbonitrile (6.80 g, 20.35 mmol) in 82 mL of N,N-dimethylformamide was added guanidine carbonate (9.17 g, 101.75 mmol). The mixture was heated to 110° C. for 18 hours under efficient stirring. Then, a further amount of guanidine carbonate (1.83 g; 20.35 mmol) was added to the mixture and heating to 115° C. was prolonged for additional 22 hours. The resulting mixture was diluted by dropwise addition of 325 mL of water over 30 minutes. The solid was isolated by filtration, washed with 100 mL of water, dried in the air and, finally, in a vacuum oven at 60° C. affording 5.58 g of product as a light brown powder. Yield=83%.

$^1$H-NMR (DMSOd$_6$), δ ppm: 6.48 (bs, 2H) 7.00-8.28 (m, 6H) 12.70 (bs, 1H).

HRMS (M+H)$^+$ calcd: 330.0308. found: 330.0317.

Step IV 5-(2-amino-pyrimidin-4-yl)-2-(2,4-dichloro-phenyl)-1H-pyrrole-3-carboxylic acid amide (I, R$_1$=R$_2$=Cl)

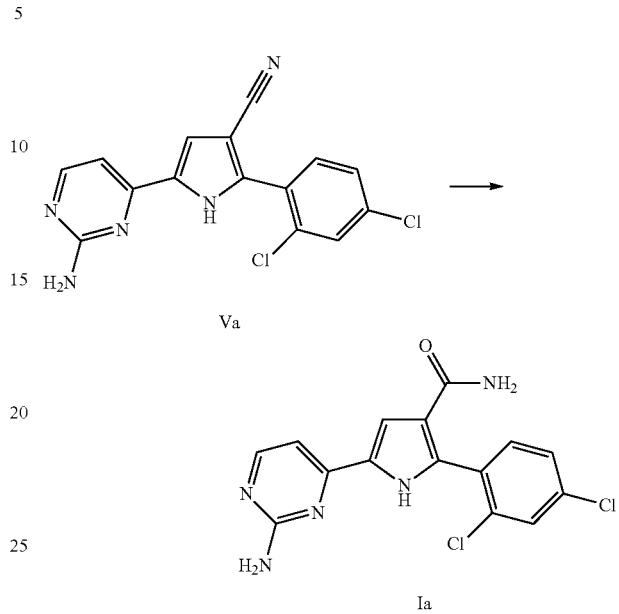

To a solution of 5-(2-amino-pyrimidin-4-yl)-2-(2,4-dichloro-phenyl)-1H-pyrrole-3-carbonitrile (210 mg, 0.636 mmol) in 1.70 mL of trifluoroacetic acid were sequentially added 0.21 mL of water and 0.42 mL of 98% sulfuric acid under efficient stirring. The mixture was allowed to stir for 8 hours at 70° C. and, then, was diluted by dropwise addition of 3 mL of water over a period of 10 minutes.

The reaction mixture was made basic (pH 10-12) by adding 30% aqueous ammonia under stirring and filtering off the free base as a precipitate. The precipitated solid was collected by filtration, washed with 1 mL of water and finally dried in a vacuum oven at 50° C. affording 186 mg of product as an off-white solid. Y=84%.

$^1$H NMR (DMSO-d$_6$/400 MHz) δ ppm 6.81 (bs, 1H) 6.95 (bs, 2H) 7.01 (d, J=5.73 Hz, 1H) 7.37 (bs, 1H) 7.46 (d, J=2.68 Hz, 1H) 7.68 (dd, J=1.77, 0.55 Hz, 1H) 8.23 (d, J=5.73 Hz, 1H) 12.17 (bs, 1H); ESI (+) MS: m/z 348 (MH$^+$).

HRMS (M+H)$^+$ calculated: 348.0414. found: 348.0415.

EXAMPLE 2

Operating as described in steps I-IV of Example 1, and starting from the appropriately substituted pyrrole of the formula II (R$_1$=R$_2$=H; R$_1$=CH$_3$, R$_2$=H; R$_1$=R$_2$=CH$_3$; R$_1$=R$_2$=F; R$_1$=Cl, R$_2$=H; R$_1$=Cl, R$_2$=F; R$_1$=Cl, R$_2$=OCH$_3$ and R$_1$=F, R$_2$=Cl.), the following compounds were obtained:

5-(2-amino-pyrimidin-4-yl)-2-phenyl-1H-pyrrole-3-carboxylic acid amide hydrochloride;

5-(2-amino-pyrimidin-4-yl)-2-o-tolyl-1H-pyrrole-3-carboxylic acid amide hydrochloride;

5-(2-amino-pyrimidin-4-yl)-2-(4-fluoro-2-methyl-phenyl)-1H-pyrrole-3-carboxylic acid amide hydrochloride;

5-(2-amino-pyrimidin-4-yl)-2-(2,3-dimethyl-phenyl)-1H-pyrrole-3-carboxylic acid amide hydrochloride;

5-(2-amino-pyrimidin-4-yl)-2-(2,3-difluoro-phenyl)-1H-pyrrole-3-carboxylic acid amide hydrochloride;
5-(2-amino-pyrimidin-4-yl)-2-(2,4-difluoro-phenyl)-1H-pyrrole-3-carboxylic acid amide hydrochloride;
5-(2-amino-pyrimidin-4-yl)-2-(2,5-difluoro-phenyl)-1H-pyrrole-3-carboxylic acid amide hydrochloride;
5-(2-amino-pyrimidin-4-yl)-2-(2-chloro-phenyl)-1H-pyrrole-3-carboxylic acid amide hydrochloride;
5-(2-amino-pyrimidin-4-yl)-2-(2-chloro-4-fluoro-phenyl)-1H-pyrrole-3-carboxylic acid amide hydrochloride;
5-(2-amino-pyrimidin-4-yl)-2-(2-fluoro-4-methyl-phenyl)-1H-pyrrole-3-carboxylic acid amide hydrochloride;
5-(2-amino-pyrimidin-4-yl)-2-(2,3-dichloro-phenyl)-1H-pyrrole-3-carboxylic acid amide hydrochloride;
5-(2-amino-pyrimidin-4-yl)-2-(2-fluoro-3-methoxy-phenyl)-1H-pyrrole-3-carboxylic acid amide hydrochloride and
5-(2-amino-pyrimidin-4-yl)-2-(2-fluoro-4-chloro-phenyl)-1H-pyrrole-3-carboxylic acid amide hydrochloride.

The invention claimed is:
1. A process for preparing a 5-(2-amino-pyrimidin-4-yl)-2-aryl-1H-pyrrole-3-carboxamides of the formula (I) or pharmaceutically acceptable salts thereof:

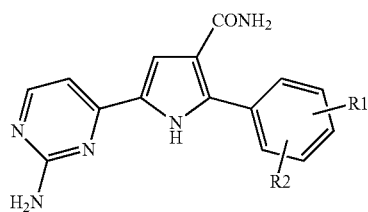

wherein $R_1$ and $R_2$ independently represent hydrogen or halogen atom or alkyl, cycloalkyl, aryl, aroyl, carboxyl esters, cyano or nitro group, which process comprises:
(a) reacting a pyrrole of the formula (II):

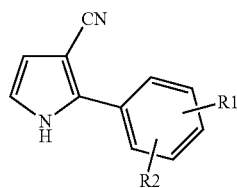

wherein $R_1$ and $R_2$ are as defined above, with acetyl chloride in the presence of a Lewis acid;
(b) reacting the resultant compound of the formula (III):

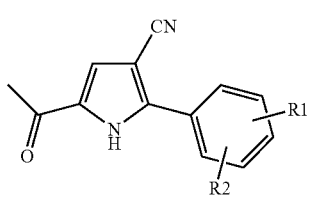

wherein $R_1$ and $R_2$ are as defined above, with a dialkyl acetal of N,N-dimethylformamide, (c) reacting the resultant enaminone of the formula (IV):

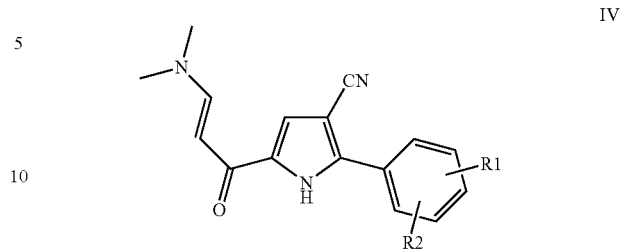

wherein $R_1$ and $R_2$ are as defined above, with guanidine or a salt thereof, and then,
(d) hydrolizing the cyano group of the resultant compound of the formula (V)

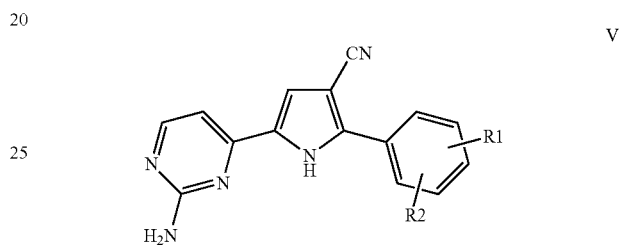

wherein $R_1$ and $R_2$ are as defined above in acidic conditions, so as to obtain the amide of the formula (I), as defined above in salt form;
and, if desired, converting the resultant salt into the free base in basic conditions.
2. A process according to claim 1 which further comprises converting the carboxamides of the formula (I) as defined in claim 1 into pharmaceutically acceptable salts.
3. A compound of the formula (III):

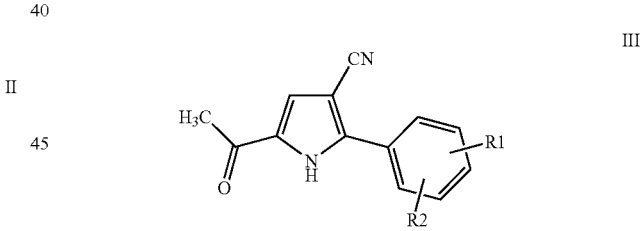

wherein $R_1$ and $R_2$ independently represent hydrogen or halogen atom or alkyl, cycloalkyl, aryl, aroyl, carboxyl esters, cyano or nitro group.
4. A process for preparing a compound of the formula (III) as defined in claim 3, which process comprises reacting a pyrrole of the formula (II):

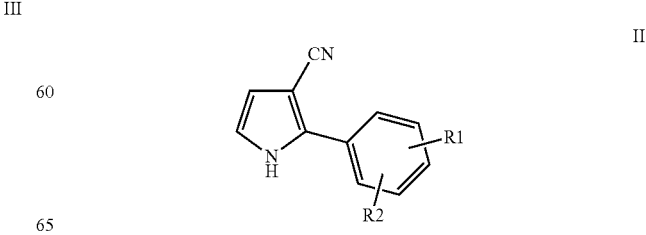

with acetyl chloride in the presence of a Lewis acid.

5. A compound of the formula (IV):

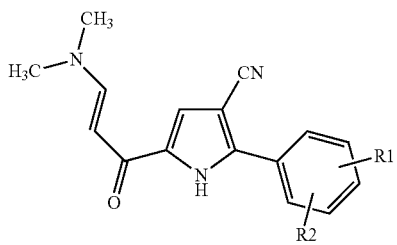

wherein $R_1$ and $R_2$ independently represent hydrogen or halogen atom or alkyl, cycloalkyl, aryl, aroyl, carboxyl esters, cyano or nitro group.

6. A process for preparing a compound of the formula (IV) as defined in claim 5, which process comprise the treatment of a compound of the formula (III):

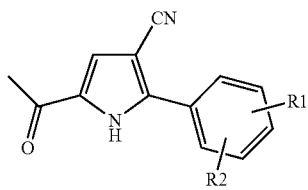

with a dialkyl acetal of N,N-dimethylformamide.

7. A compound of the formula (V)

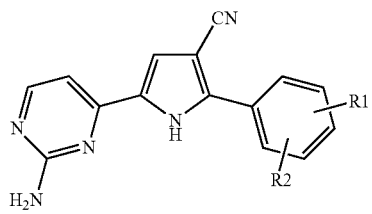

wherein $R_1$ and $R_2$ independently represent hydrogen or halogen atom or alkyl, cycloalkyl, aryl, aroyl, carboxyl esters, cyano or nitro group.

8. A process for preparing a compound of the formula (V) as defined in claim 7, which process comprises reacting a compound of the formula (IV):

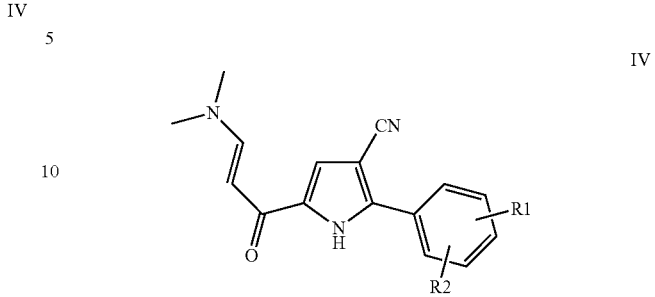

with guanidine or a salt thereof.

9. A process according to claim 1 or claim 4, characterized in that the acylation of a compound of the formula (II) to give a compound of the formula (III) is performed with acetyl chloride in the presence of a Lewis acid, operating under cooling at a temperature of from −5° C. to 0° C., or at room temperature, in an anhydrous organic solvent.

10. A process according to claim 1 or claim 6, characterized in that the conversion of a compound of the formula (III) as defined in claim 1 into the enaminone of the formula (IV) as defined in claim 1 is carried out using a dialkyl acetal of N,N-dimethylformamide, at a temperature between room and reflux temperature, in an organic solvent.

11. A process according to claim 1 or claim 8, characterized in that the conversion of a compound of the formula (IV) as defined in claim 1 into a compound of the formula (V) as defined in claim 1 is carried out by reaction with guanidine, guanidine hydrochloride or guanidine carbonate at a temperature of from 80° C. to 130° C., in an organic solvent.

12. A process according to claim 1, characterized in that the hydrolysis in acidic condition of the nitrile derivative of the formula (V) as defined in claim 1 to yield the carboxamides of the formula (I) as defined in claim 1 is performed in glacial acetic acid or trifluoroacetic acid and concentrated sulfuric acid, optionally in the presence of water, at a temperature of from room temperature to 120° C.

13. A process according to claim 2, characterized in that the conversion in basic conditions of the salt of the carboxamides of the formula (I) into the free base is performed dissolving the salt in a suitable solvent, and adding a base, in water, stirring for a convenient period of time, and filtering off the free base as a precipitate.

* * * * *